United States Patent
Sawatari et al.

[11] Patent Number: 5,987,995
[45] Date of Patent: Nov. 23, 1999

[54] FIBER OPTIC PRESSURE CATHETER

[75] Inventors: Takeo Sawatari, Bloomfield Hills; Yuping Lin, Troy; Philip A. Gaubis, Walled Lake, all of Mich.

[73] Assignee: Sentec Corporation, Walled Lake, Mich.

[21] Appl. No.: 08/895,727

[22] Filed: Jul. 17, 1997

[51] Int. Cl.⁶ .............................. G01L 9/00; G01L 7/08; A61B 5/02
[52] U.S. Cl. .............................. 73/705; 73/715; 128/667; 128/675
[58] Field of Search ............................. 600/488; 73/705, 73/715; 250/231.19; 128/667, 672

[56] References Cited

U.S. PATENT DOCUMENTS

| | | | |
|---|---|---|---|
| 4,135,601 | 1/1979 | Tsukagoshi et al. | 181/167 |
| 4,589,286 | 5/1986 | Berthold, III | 73/715 |
| 4,611,600 | 9/1986 | Cohen | 73/705 |
| 4,667,069 | 5/1987 | Cholkeri | 200/83 |
| 4,691,708 | 9/1987 | Kane | 73/705 |
| 4,924,870 | 5/1990 | Wlodarczyk et al. | 73/705 |
| 4,924,877 | 5/1990 | Brooks | 128/667 |
| 4,926,696 | 5/1990 | Haritonidis et al. | 73/705 |
| 4,927,461 | 5/1990 | Ciloglu et al. | 75/254 |
| 4,942,767 | 7/1990 | Haritonidis et al. | 73/705 |
| 4,991,590 | 2/1991 | Shi | 128/667 |
| 5,018,529 | 5/1991 | Tenerz et al. | 128/667 |
| 5,275,053 | 1/1994 | Wlodarczyk et al. | 73/705 |
| 5,365,789 | 11/1994 | Totterdell et al. | 73/721 |
| 5,425,371 | 6/1995 | Mischenko | 73/705 |
| 5,485,741 | 1/1996 | Madison | 73/4 R |
| 5,633,552 | 5/1997 | Lee et al. | 310/311 |

*Primary Examiner*—George Dombroske
*Assistant Examiner*—Robin Clark
*Attorney, Agent, or Firm*—Dykema Gossett PLLC

[57] ABSTRACT

A fiber optic pressure catheter includes a light source, an optical fiber coupled to receive light from the light source and a sensor head that is optically coupled to the optical fiber. The sensor head has a housing defining a chamber coupled to an end of the optical fiber opposite the light source. The housing has an opening which is enclosed by a membrane. The membrane is responsive to pressure differentials between the chamber and outside the sensor head. A resilient ribbon is coupled within the chamber and has a first end fixedly coupled to a support. The ribbon has a second end that is movable in front of the optical fiber. The ribbon is mounted so that the middle portion of the ribbon touches the membrane and is biased by the membrane in response to various pressure differentials. Thus, various amounts of light are reflected back into the optical fiber based on the amount of pressure at the membrane. A detection system is optically coupled to the optical fiber which determines the pressure at the sensor head from the contrast of spectral fringes of light created by an optical coating on the end of the optical fiber and the light reflecting from the ribbon.

21 Claims, 4 Drawing Sheets

FIBER OPTIC PRESSURE CATHETER

STATEMENT REGARDING FEDERALLY FUNDED RESEARCH

This invention was made with Government support under Grant Number 5R44HL47277 awarded by the National Institute of Health. The Government has certain rights in this invention.

BACKGROUND OF THE INVENTION

The present invention relates generally to a pressure sensor and, more specifically, to a fiber optic pressure sensor having a relatively small diameter so that the pressure sensor is suitable for insertion into the human body particularly in patients such as children having narrow arteries.

After open heart surgery, the blood pressure of the patient must be monitored for several days, typically 72 hours, after surgery. It is necessary to monitor both the diastolic and systolic blood pressure inside the patient's heart chambers to monitor for possible clogging of the arteries. After brain surgery, continuous monitoring of brain fluid pressure is also required. For children in particular, monitoring fluid pressures in the brain and in their arteries may be impossible using conventional pressure sensors since conventional pressure sensors have a relatively large diameter and would constrict the flow of the fluid being measured.

Electronic pressure catheters exist that may be used to measure the fluid pressures in a human body. For example, Millar's 2 French diameter unit which has a relatively small diameter is very expensive. Other less expensive electronic catheters such as Millar's 9 French is 3 mm in diameter.

Other devices employ remote measuring in which pressure tubing and flush devices are required. Remote measurement requires the high cost of surgery and discomfort to the patient. Other known pressure sensors include fiber optic devices. Fiber optics have the ability to bend easily and conform to the blood vessels while they can be manufactured out of bio-compatible materials. Known fiber optic pressure catheters use small moving mechanical parts. Commonly, the mechanical part is a optically reflective membrane. The membrane forms a mirror with respect to the light emitted from the end of the optical fiber. The membrane is stressed and deformed as a function of the pressure differential applied to it. As the deformation of the membrane continues, the amount of light reflected back into the fiber is a function of the applied pressure.

One problem with such sensors however, is that the membranes must be precision mounted in the sensor head. Because these membranes are on the order of one micron thick with a diameter of about 700 microns, it is very difficult to mount them in the sensor head without introducing significant mechanical hysteresis and without creating a tendency to buckle. Although some of the hysteresis effect may be corrected by software, production yield is very low. Therefore, such units are restrictively high in price which limit its applications. Even so, the smallest known sensor has a relatively large diameter and cannot be used for children and infants.

SUMMARY OF THE INVENTION

It is therefore an object of the invention to provide a pressure sensing catheter having a very small diameter and is suitable for remaining in a patient for a number of days.

In one embodiment of the invention, a pressure sensor includes a light source, an optical fiber coupled to receive light from the light source, and a sensor head that is optically coupled to the optical fiber. The sensor head has housing defining a chamber coupled to an end of the optical fiber opposite the light source. The end of the optical fiber opposite the light source has an optical coating. The housing has an opening. A membrane encloses the opening. The membrane is responsive to pressure differentials between the chamber and outside the sensor head. A resilient ribbon is coupled within the chamber and has a first end fixedly coupled to a support. The ribbon has a second end that is movable in front of the optical fiber. The ribbon is mounted so that the middle portion of the ribbon touches the membrane and is biased by the membrane in response to various pressure differentials. Thus, various amounts of light are reflected back into the optical fiber based on the amount of pressure at the membrane. A detection system is optically coupled to the optical fiber which determines the pressure at the sensor head from a change in spectral fringe contrast. The spectral fringes are formed by the optical coating placed at the end of the optical fiber and the contrast of the fringes as varied by the ribbon.

In one embodiment of the invention, the optical fiber has a loop along its length in order to increase the robustness of the system. By bending the optical fiber higher order modes of light propagating down the fiber are leaked out. Because these higher order modes of light are leaked out, the system is less susceptible to intensity fluctuation and other light source characteristic changes during normal use. The light remaining in the fiber after the bend tends to remain in the optical fiber.

One advantage of the present invention is that a catheter using pressure sensor may be manufactured at a relatively low cost compared to previously known pressure sensors. This is due to the membrane not being optically active in the sensor.

Another advantage of the present invention is that the pressure sensors may be calibrated at a central location, e.g., at the manufacturing facility. The connector may include a memory chip that stores the calibration data therein. Upon connection to a computer used for monitoring pressure, the data from the memory chip may be loaded into memory and thus accurate calibration data may be used in the pressure calculations.

Other advantages of the present invention include the small diameter of the sensor head, the stability of the sensor for long periods of time at human body temperatures, and the high sensitivity of the sensor head. The sensitivity has been determined to be better than 2 mmHg for pressures ranges of between 0 and 300 mmHg. The response time is no more than 20 msec.

BRIEF DESCRIPTION OF THE DRAWINGS

Other features and advantages of the present invention will become apparent from the following detailed description which should be read in conjunction with the drawings in which.

DETAILED DESCRIPTION OF THE PREFERRED EMBODIMENT

Figure 1:
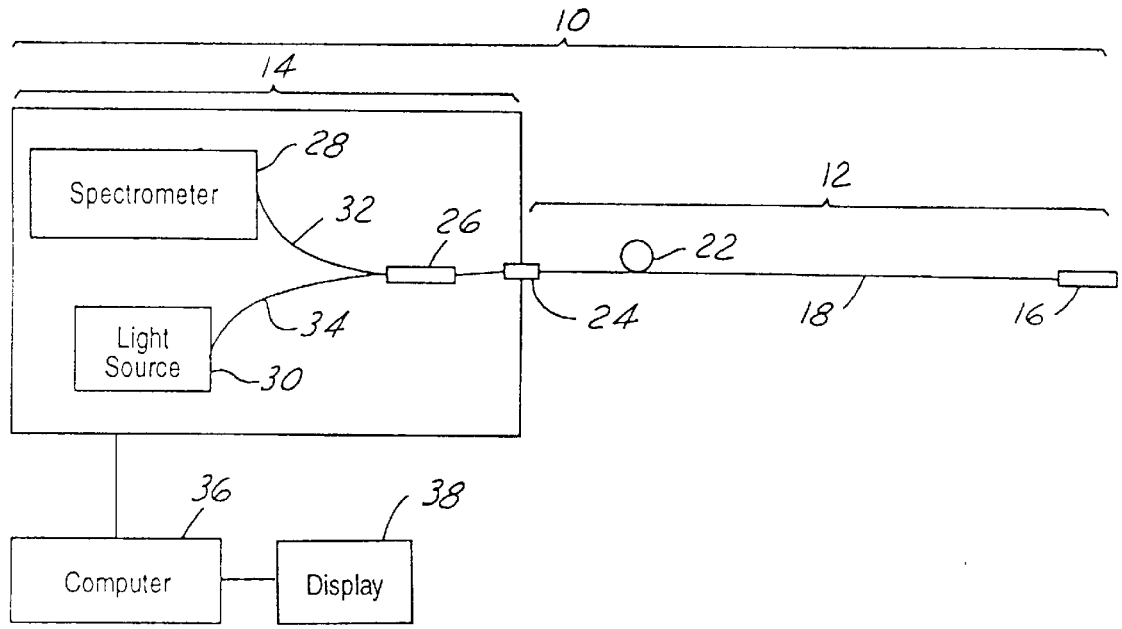
FIG. 1 is a diagrammatic representation of a pressure sensing system according to the present invention.

Referring now to the drawings like reference numerals are used to identify identical components in the various views. Although the invention will be illustrated in the context of a fiber optic sensor suitable for use in a human body, it will be appreciated this invention may be used with other applications requiring pressure sensing.

Referring now to FIG. 1, a pressure sensing system 10 has a sensor unit 12, a light transmitting and receiving unit 14. Sensor unit 12 extends to the location in which the pressure is to be measured. Sensor unit 12 provides a light spectral fringe pattern to light transmitting and receiving unit 14. Light transmitting and receiving unit 14 converts the spectral fringe pattern into a pressure reading.

Sensor unit 12 generally comprises a sensor head 16, an optical fiber 18 and a sensor unit connector 24. Sensor head 16 is located at the position where the pressure is to be determined. Sensor head 16 may, for example, be placed in a human artery to measure blood pressure or placed within the brain to measure fluid pressure. Optical fiber 18 is connected between sensor head connector 22 and sensor head 16.

Light transmitting and receiving unit 14 has a mating half of sensor unit connector 24, an optical coupler 26, a spectrometer 28, a light source 30, an optical fiber 32 and an optical fiber 34. Optical fiber 34 is used to connect optical coupler 26 to light source 30.

Optical coupler 26 is used to couple light generated from light source 30 which is to be transmitted to sensor head 16 through optical fiber 18. Optical coupler 26 is also used as a beam splitter to send the light returned by sensor head 16 to spectrometer 28.

Spectrometer 28 is used to analyze the light received from sensor head 16. Spectrometer 28 may divide the light up into its wavelength components. Spectrometer 28 preferably uses a linear detector such as a series of charge coupled devices (CCD). Spectrometer 28 converts the detected light signal from sensor 16 into a desirable output format such as digital signals.

Light source 30 is preferably a wide band light source such as a white light source. One example of a desirable white light source is a tungsten-halogen source.

Light transmitting and receiving unit 14 may also have a computer 36 associated therewith. Computer 36 is used to perform mathematical calculations further described below. With the digitized output of spectrometer 28, a display 38 may be used to display the pressure as calculated by computer 36 of the sensor head 16. Spectrometer 28 and optical coupler 26 may be contained on a computer board which is inserted into computer 36. Such a light digitizer is manufactured by Ocean Optics. It is also preferred that light source 30 is contained on such a computer board. However, a standardized board contained a spectrometer and light source was not known at the time of this application.

Figure 2:
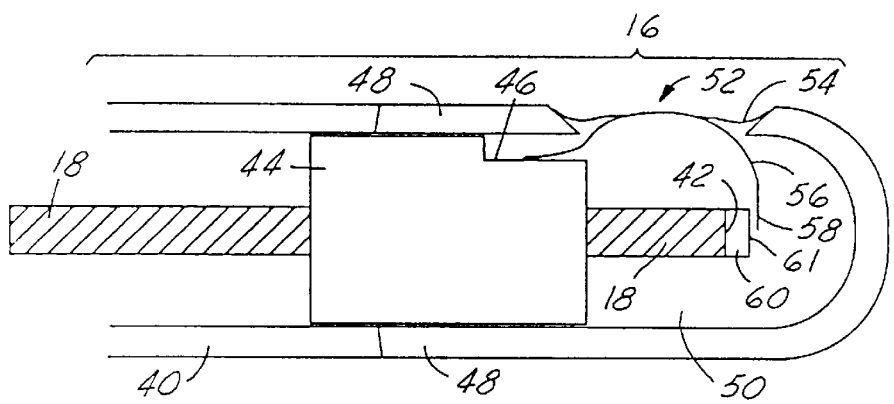
FIG. 2 is a cross-sectional view of a pressure sensor according to the present invention.

Referring now to FIG. 2, one embodiment of a sensor head 16 is shown coupled to an optical fiber 18 having a casing 40 surrounding optical fiber 18. Casing 40 provides protection and stiffness for optical fiber 18. Casing 40 preferably extends from sensor head 16 to connector 24. Optical fiber 18 has an end 42 that extends beyond casing 40. The end 42 is preferably polished to be optically flat.

A support tube 44 is coupled to optical fiber 18 and casing 40. Support tube 44 may be welded or cemented in place for example with a general purpose adhesive, such as SUPER GLUE brand adhesive. Support tube 44 has a flat portion 46 which is cut out of support tube 44. Support tube 44 is preferably affixed to optical fiber 18 so that leakage between optical fiber 18 and support tube 44 maintains the constant atmospheric pressure inside the cavity 50. Support tube 44 is preferably made from a plastic or metal material.

A housing 48 is coupled to support tube 44. Housing 48 defines a cavity 50 which encloses end 42 of optical fiber 18. Housing 48 is made of a plastic or metallic material. Housing 48 is coupled to support tube 44 by welding or cement. The diameter of housing 48 is less than one millimeter.

Housing 48 has an opening 52 through to cavity 50. Opening 52 has a membrane 54 that encloses opening 52. Membrane 54 is preferably made of a flexible material such as polyurethane. Membrane 54 flexes in response to pressures outside sensor head 16 since cavity 50 is supported at support tube 44 and by membrane 54. Membrane 54 may have a coating of friction reducing material such as a powder of boron nitrate on the inside surface.

A ribbon 56 is attached to flat portion 46 of support tube 44. Ribbon 56 is preferably affixed to flat portion 46 by welding or cementing. Ribbon 56 is made of a reflective metallic material that is oxidation resistant. It is also preferred that the metallic material of ribbon 56 have a large linear elastic range, good fatigue resistance, and a low thermal coefficient of expansion. Ribbon 56 must be also capable of retaining a shape once formed. One suitable material for ribbon 56 is KOVAR® brand alloyed metal. Only one end of ribbon 56 is coupled to support tube 44. The middle portion of ribbon 56 is shaped so that it contacts membrane 54 and a reflective end 58 is capable of being flexed in front of end 42 of optical fiber 18. Reflective end 58 may be flat, i.e., parallel with end 42, or concave. Reflective end 58 is preferably polished to increase reflectance. As pressure outside sensor head 16 changes, membrane 54 biases ribbon 56 so that various amounts of reflective end 58 extend in front of end 42.

A portion of the light from light source 30 never leaves optical fiber 18. That is, the light reflects from end 42 and travels back through optical fiber 18. To increase and generate a desired pattern of the reflectance of end 42, an optical thin film coating 60 may be formed on end 42. Coating 60 also allows light to pass through it. Light contacting the end of coating 61 both passes through the coating 60 and reflects back into the end of the optical fiber. Coating 60 is separated from reflective end 58 of ribbon 56 by a predetermined distance. Coating 60 preferably has a high refractive index. Optical coating 60 may be, for example, ZnS or $TiO_2$ and the thickness may be 0.7 to 3 microns but is preferably about 2 microns.

As pressures increases, the amount of reflective end 58 in front of optical fiber 18 is varied. The amount varies from no reflective end in front of optical fiber to reflective end 58 fully blocking optical fiber 18. As shown, reflective end 58 is partially in front of end 42 of optical fiber 18.

Figure 3:
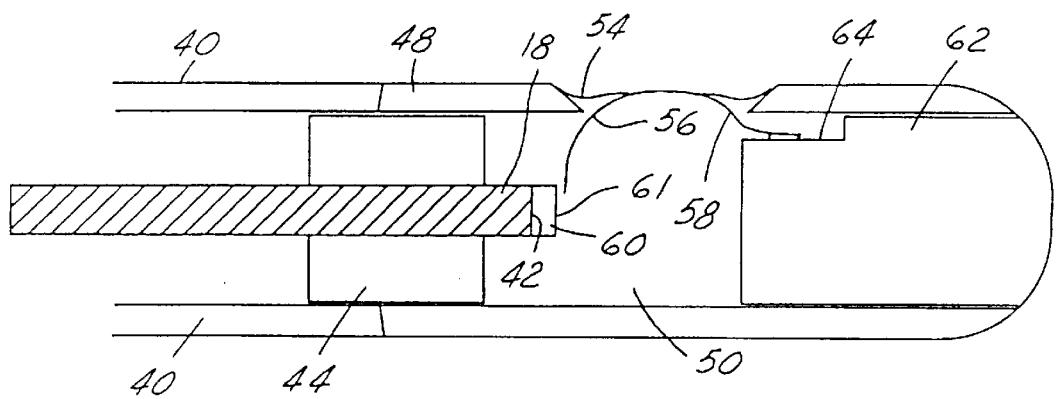
FIG. 3 is a cross-sectional view of an alternative configuration for a pressure sensor head.

Referring now to FIG. 3, support tube 44 does not have a flat portion 46 to support ribbon 56 as it does in FIG. 2. Support tube 44 does still join casing 40 and housing 48. A support rod 62 has a flat portion 64 used to mount ribbon 56 thereto similar to that of flat portion 46 above. Support rod 62 is opposite end 42 of optical fiber 18. In this configuration, ribbon 56 also extends in front of end 42 of optical fiber 18. Operation of the configuration of FIG. 3 is nearly identical to that of FIG. 2 as will be described further below.

Figure 4:
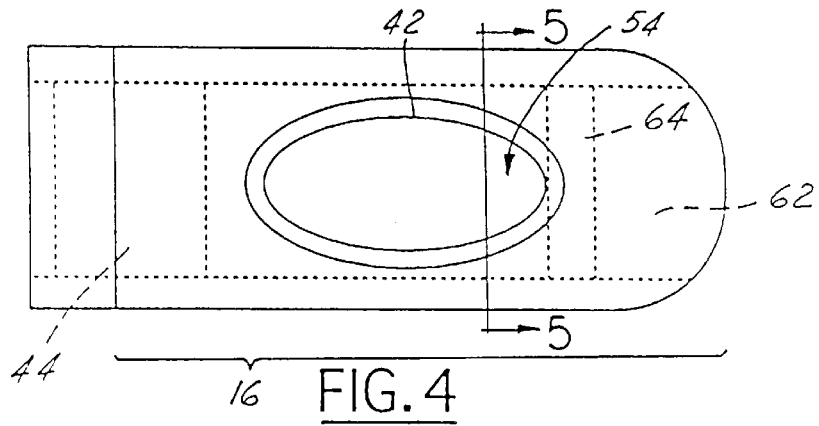
FIG. 4 is a top view of a pressure sensor head.

Referring now to FIG. 4, a top view of sensor head 16 of FIG. 3 is shown. Opening 52 is preferably an elongated shape such as an oval. However, other shapes such as rectangular or circular may be used. Within sensor head 16, the relative positions of support rod 62 with flat portion 64 and support tube 44 are shown in hidden lines.

Figure 5:
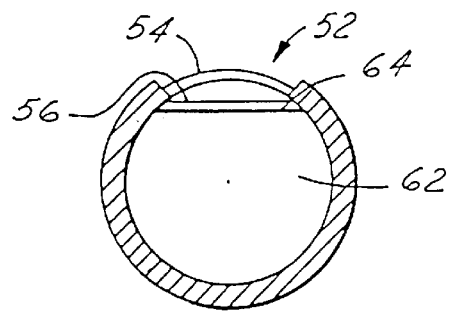
FIG. 5 is a cross-sectional view of as sensor head along line 5—5 of FIG. 4.

Referring now to FIG. 5, a cross-sectional view of FIG. 4 is shown. Ribbon 56 is shown mounted to flat portion 64 of support rod 62.

Figure 6:
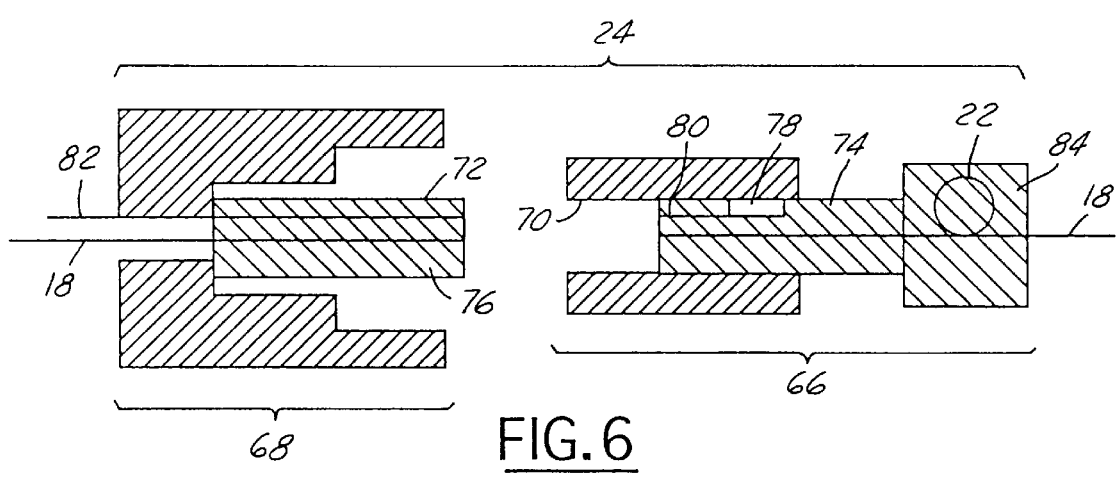
FIG. 6 is a cross-sectional view of a connector according to the present invention.

Referring now to FIG. 6, sensor unit connector 24 is shown in more detail. Connector 24 preferably has a male portion 66 and a female portion 68. Male portion 66 is used to connect optical fiber 18 and therefore sensor head 16 to light transmitting and receiving unit 14. Female portion 68 may be a connector mounted on a computer board. Male portion 66 may have threads 70 which are used to couple to threads 72 of female portion 68. It is preferred that both sets of threads 70 and 72 are formed of metallic material. Male portion 66 may have an optical fiber holder 74 which is connected to thread 70. Female portion 68 may also have a holder 76 to hold optical fiber. In day to day use, male portion 66 will be associated with a single sensor head and its associated optical fiber. Male portion 66 can be removed to change sensor head 16. When sensor head 16 is changed, a new male portion optical fiber and sensor head are all replaced.

Male portion 66 contains a memory chip 78. Memory chip 78 is used to store calibration data for the particular sensor head as will be further described below. Memory chip 78 is coupled through an electrode 80 in male portion 66. When male portion 66 is connected to female portion 68, it is preferably connected to an electrode 82 in female portion 68. When male portion 66 is connected to female portion 68, the information contained in memory chip 78 is used by computer 36 to calculate the pressure based on the contrast change of spectral fringe pattern created in sensor head 16. Threads 70 and threads 72 are preferably formed of metallic material so that the metal may act as a ground for memory chip 78. Memory chip 78 may be a read only type memory; however, memory chip may also be a RAM type memory so that the memory may be updated. For example, calibration data stored in memory chip 78 may be renewed each time a re-calibration sequence is run.

In addition, loop 22 may be included in a loop portion 84 of male portion 66. Loop portion 22, however, may be included anywhere along optical fiber 18 between spectrometer 28 and sensor head 16. Loop portion 84 may be integrally molded within male portion 66.

When male portion 66 and female portion 68 are connected, coded numbers that specify sensor offset values and other calibration data for particular sensor unit are retrieved from memory chip 78.

In operation, a pressure differential between the interior of housing 48 and outside sensor head 16 causes membrane 54 to flex. This causes end 58 of reflective ribbon 56 to move in front of end 42 of optical fiber. Thus, as the pressure changes various amounts of light are reflected by end 58 of ribbon 56.

Figure 7:
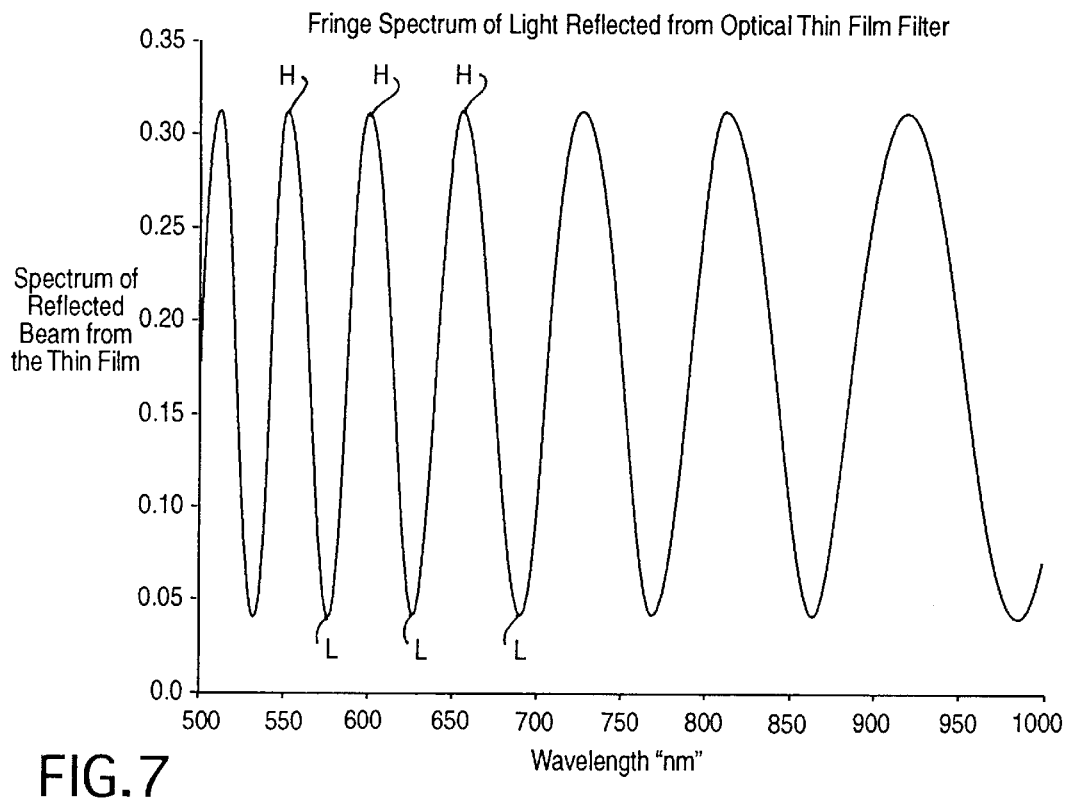
FIG. 7 is a plot of a spectrum reflected from the thin film on the optical fiber.

Light generated from light source 30 propagates down optical fiber 34 through optical coupler 26 through connector 24 and to sensor head 16 through optical fiber 18. A portion of the light is reflected back into optical fiber 18 by end 42. Another portion of light beam reflects from end 61 of optical coating 60. The two beams recombine to form a return beam. The return beam of the light from coating 60 returns through loop 22, connector 24, optical coupler 26, and through optical fiber 32 to spectrometer 28. In analyzing the reflected light, the spectrum of the light detected by the spectrometer may be normalized by a spectrum corresponding to zero pressure. A normalized spectrum of light reflected form is shown in FIG. 7. Peaks of light are represented by H and valleys are represented by L.

Figure 8:
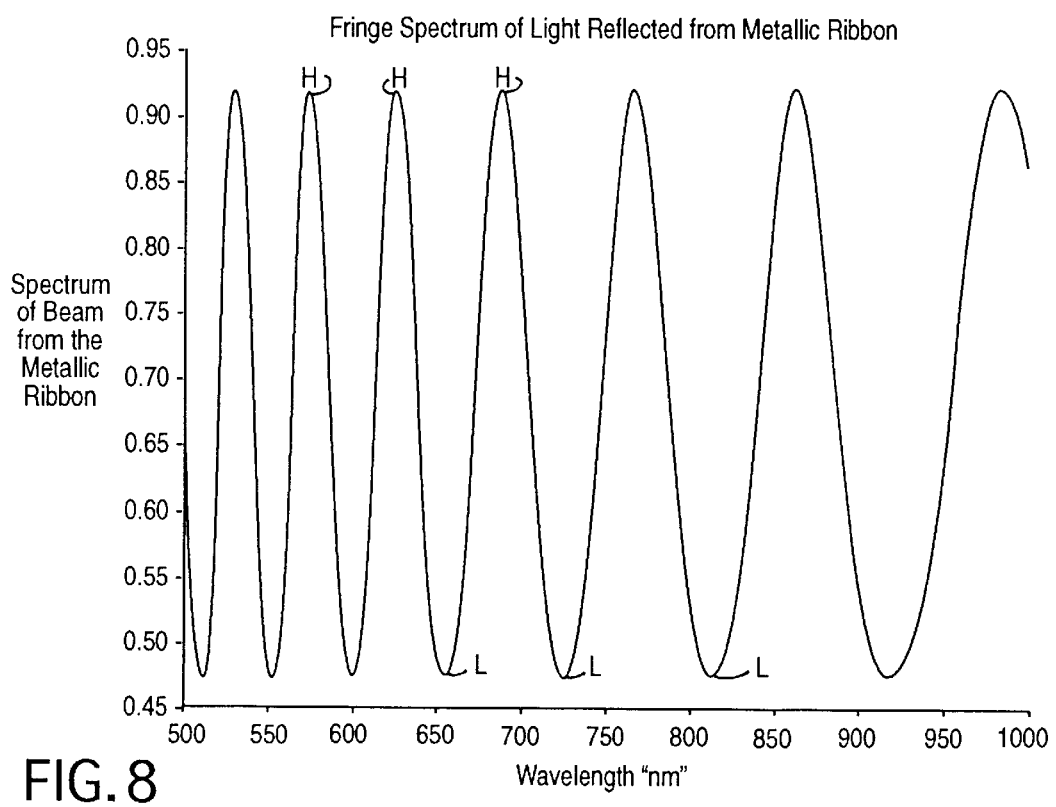
FIG. 8 is a plot of a spectrum reflected from the ribbon surface.

Another portion of light incident upon end 61 of coating 60 is transmitted through coating 60 to reflective end 58 of ribbon 56. A portion of the light reflected from reflective end 58 re-enters fibers through coating 60. The fringe spectrum reflected from ribbon 56 is shown in FIG. 8. It should be noted that the fringe spectrum of the re-entered light is a "complement" of the beams reflected at coating 60 of FIG. 7. Peaks H of FIG. 7 become valleys L of FIG. 8 and valleys L of FIG. 7 become peaks H of FIG. 8. Both beams become superimposed and travel through optical fiber 18 to spectrometer 28. As the pressure varies the amount of reflective end 58 covering the end of optical fiber 18 varies. This causes a change in the fringe contrast in the detected fringe spectrum. Contrast C is defined as:

$$C=(H-L)/(H+L)$$

The spectrum of light reflect from thin film coating 60 remains constant. The amount reflected from ribbon 56 varies as the amount of reflective end 58 is moved in front of end 42. The spectrometer 28 receives the fringe patterns that have been added together. The contrast is independent of the light source spectrum distribution and is, at least in the first order, independent of changes of the light source spectrum caused by bending of the optical fiber, alignment changes in the coupler and other optical opponents. The calculated pressure is independent of the spectrum. So along the spectrum the pressure can be repetitively determined for more accuracy. In the present invention the time required for such calculations is less than one millisecond, i.e., one Khz. The desire frequency response for a pressure catheter is in the order of 100 Hz. During the calculation the peaks and valleys of the entire spectral range are integrated in order to determine a pressure. The integrated values are compared to the calibration data retrieved from memory chip 78 in male portion of sensor unit connector 24.

The spectrum normalization described in the above paragraphs is not necessary in actual data processing. A quantity equivalent to the contrast (C) given in the above equation can be calculated from unnormalized spectrum data where H or L is the spectrum value of a wavelength which corresponds to high or low reflectance of the coating. For a given coating of a known thickness and refractive index, the wavelengths at which the reflectance becomes high or low is predetermined and unchanged.

It should be noted that the pre-bending or loop 22 which has been placed along the length of optical fiber 18, has the effect of leaking out higher modes of light propagating through the fiber. The modes which have not leaked out at the loop 22 tend to remain within the fiber and propagate through it. Thus, these higher order modes of light which varies when fiber bends do not factor into the calculations performed as described above.

Combined use of the above explained methods of (1) the contrast measurement using coating 60 and (2) fiber loop 22, enhances important characteristics of a high performance sensor, which is that the sensor should be only sensitive for the pressure change and insensitive to fiber bending and source intensity fluctuation.

Figure 9:
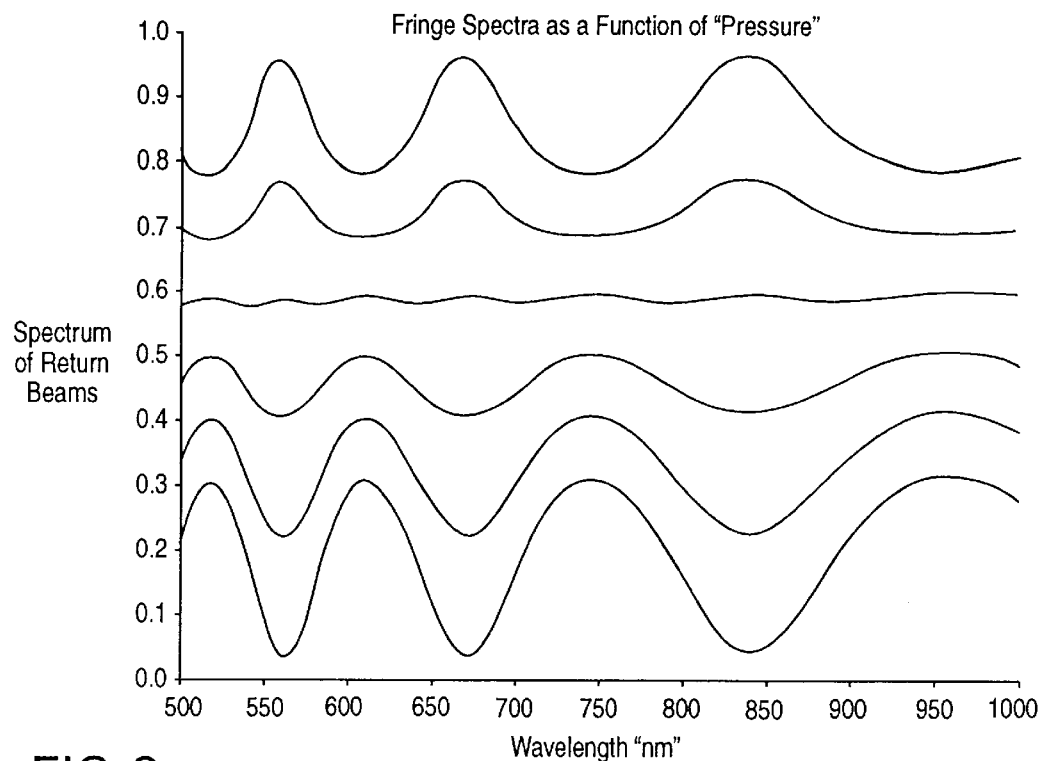
FIG. 9 is a plot of a spectrum contrast variation as a function of pressure.

Referring now to FIG. 9, various superimposed fringe spectra are shown as a function of pressure. The bottom plot is a plot wherein the reflective end is not covering any of optical fiber 18. As the pressure increases, reflective end 58 covers more and more of optical fiber 18 causing the fringe spectra to change. The top plot is a fully covered which corresponds to the maximum calibrated range for the pressure sensor. The middle plots have various degrees of ribbon in front of optical fiber.

The DC signal component of the fringe as shown in FIG. 9 drift when in constant use depending on the materials selected. The amount of drift may be readily determined and placed into the computer 36 to compensate for the drift in the calculations. It has been calculated that approximately 5 mmHg of drift is present over about six hours. The drift is caused by characteristic changes in the polyurethane membrane 54 when it is stressed for a long period of time. Because this drift is constant, computer 36 may easily compensate for the drift.

Figure 10:
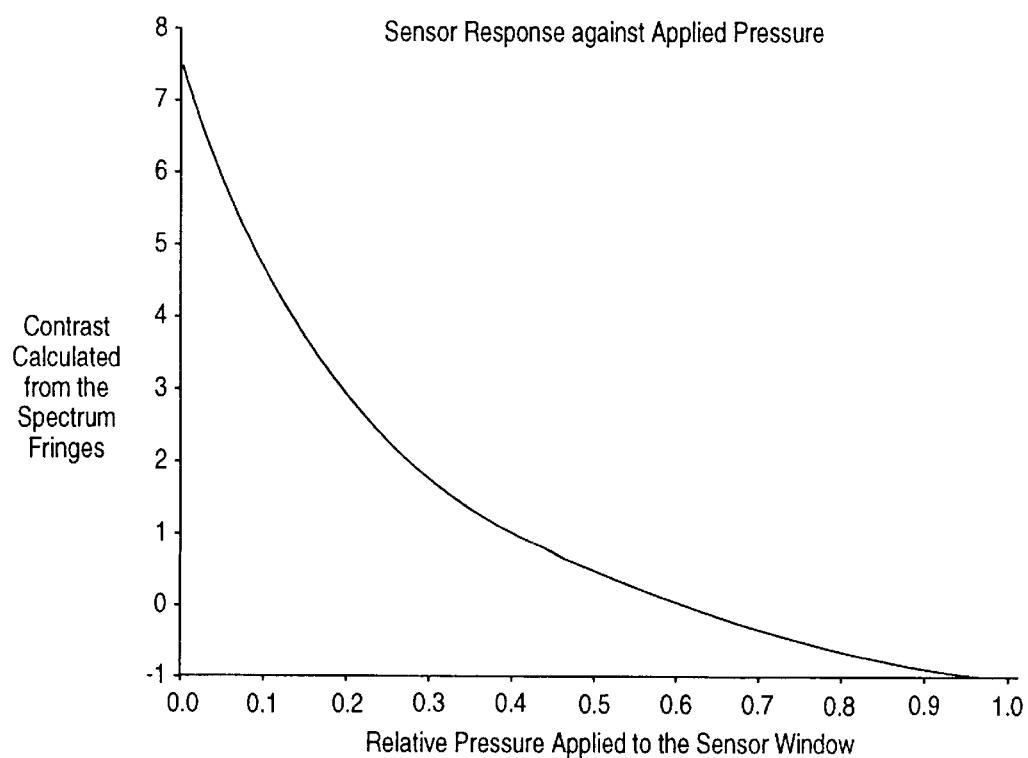
FIG. 10 is a plot of contrast versus pressure applied to the sensor window.

Referring now to FIG. 10, a plot of contrast relative to pressure applied to the membrane is shown. As the plot demonstrates, the contrast decreases as the pressure applied to the membrane increases.

While the best mode for carrying out the present invention has been described in detail, those familiar with the art to which this invention relates will recognize various alternative designs and embodiments for practicing the invention as defined by the following claims.

What is claimed is:

1. A pressure sensing system comprising:
   a broadband light source;
   an optical fiber configured to receive light from said light source at a first end and having a second end opposite said first end, said fiber including a first end surface at said second end thereof, said fiber further including an optical thin film at said second end thereof and having a second end surface;
   a sensor head coupled to said optical fiber, said sensor head including (i) a sensor housing defining a chamber and having an opening therethrough; (ii) a support coupled in said housing; (iii) a membrane enclosing said opening and movable in response to changes in pressure; and, (iv) a ribbon having a first end fixed to said support and a second end having a reflector surface adjacent said second end surface of said thin film, said ribbon being mounted such that a central portion thereof engages said membrane wherein said movements of said membrane cause corresponding movements of said reflector surface in a direction substantially parallel to said first end surface; and,
   a detection system optically coupled to said optical fiber configured to determine a pressure at said sensor head from a spectral fringe pattern, said spectral fringe pattern formed by a first light beam, generated by said reflector surface responsive to said light and said movements of said reflector surface, superimposed on a second light beam generated by said first and second end surfaces responsive to said light.

2. The pressure sensing system of claim 1 wherein said detection system further includes means for determining a contrast of said spectral fringe pattern and converting said contrast to said pressure.

3. The pressure sensing system of claim 1 wherein said first end of said optical fiber includes a first connector, said first connector having a memory containing calibration data related to said sensor head.

4. The pressure sensing system of claim 3 further comprising a second optical fiber coupled to receive light from said light source at a first end thereof, and having a second connector coupled thereto at a second end thereof, said second connector being configured to matingly engage said first connector such that said first and second optical fiber are optically coupled.

5. The pressure sensing system of claim 4 wherein said memory is electrically coupled to said detection system through an electrical conductor when said first and second connectors are coupled together.

6. A pressure sensing system as recited in claim 1, wherein said first end surface is polished optically flat.

7. A pressure sensing system as recited in claim 1, wherein said optical thin film has a high refractive index.

8. A pressure sensing system as recited in claim 1, wherein said optical thin film is one from the group consisting of zinc sulfide and titanium dioxide.

9. A pressure sensing system as recited in claim 1, wherein said optical fiber has a loop formed therein.

10. A pressure sensing system as recited in claim 1, wherein said reflector surface of said ribbon is substantially parallel to said second end surface.

11. A pressure sensing system as recited in claim 1, wherein said membrane is formed of polyurethane.

12. A pressure sensing system as recited in claim 1, wherein an inside of said membrane has a friction reducing layer.

13. A pressure sensing system as recited in claim 12, wherein said friction reducing layer comprises boron-nitride.

14. A pressure sensing system as recited in claim 1, wherein said ribbon is formed of a metallic material having a low coefficient of thermal expansion, a large linear elastic range and good fatigue resistance.

15. A pressure sensing system as recited in claim 14, wherein said metallic material comprises KOVAR® alloyed metal.

16. A pressure sensing system as recited in claim 1, wherein said broadband light source comprises a white light source.

17. A pressure sensing system as recited in claim 16, wherein said white light source comprises a tungsten-halogen source.

18. A pressure sensing system as recited in claim 1, further comprising a display terminal coupled to said detection system for displaying said pressure.

19. A pressure sensing unit comprising:
   an optical fiber having a first end surface formed at a first end, said fiber further having a second end, said fiber having an optical coating on said first end surface wherein said optical coating has a second end surface, said fiber further having a connector portion coupled to said second end of said optical fiber;
   a sensor head coupled to said first end of said optical fiber and including (i) a sensor housing defining a chamber, said housing having an opening; (ii) a support coupled in said housing; (iii) a membrane portion enclosing said opening, said membrane responsive to pressure changes; and, (iv) a reflective ribbon having a first end fixedly coupled to said support and a second end having a reflector surface moveable in front of said second end surface in a direction substantially parallel to said second end surface, said ribbon being mounted so that a middle portion thereof engages said membrane and is biased by said membrane in response to said pressure changes; and, a detection system coupled to said optical fiber configured to determine a pressure at said sensor head from a spectral fringe pattern, said spectral fringe pattern formed by a first light beam, generated by said reflector surface responsive to a broadband light and said pressure changes, superimposed on a second light beam generated by said first and second end surfaces responsive to said broadband light.

20. A method for determining a pressure comprising the steps of:

transmitting broadband light in an optical fiber to a sensor head;

reflecting a first portion of the light from a first end surface of the optical fiber;

reflecting a second portion of the light from an optical coating proximate to the first end surface of the optical fiber;

reflecting a third portion of the light from a movable end of a reflective ribbon mounted within the sensor head;

moving the ribbon by various amounts in front of and in a direction substantially parallel to the first end surface of the optical fiber, said various amounts corresponding to various pressures;

generating a spectral fringe pattern from a combination of the first portion of the light, the second portion of the light, and the third portion of the light;

retrieving calibration data from a memory;

calculating a contrast of the spectral fringe pattern; and, converting the calculated contrast to a pressure using the calibration data.

21. A method for determining a pressure as recited in claim 20, wherein prior to said step of moving the ribbon, said method further comprising the step of:

moving a membrane coupled to the ribbon on the sensor head in response to said various pressures.

* * * * *